(12) United States Patent
Suda et al.

(10) Patent No.: US 9,890,370 B2
(45) Date of Patent: Feb. 13, 2018

(54) HYPERTHERMOSTABLE ENDOGLUCANASE

(71) Applicant: HONDA MOTOR CO., LTD., Tokyo (JP)

(72) Inventors: Migiwa Suda, Kisarazu (JP); Jiro Okuma, Wako (JP); Asuka Yamaguchi, Tokyo (JP); Yoshitsugu Hirose, Wako (JP); Yasuhiro Kondo, Kawagoe (JP); Masaru Sato, Kisarazu (JP); Daisuke Shibata, Kisarazu (JP)

(73) Assignee: HONDA MOTOR CO., LTD., Tokyo (JP)

( * ) Notice: Subject to any disclaimer, the term of this patent is extended or adjusted under 35 U.S.C. 154(b) by 0 days.

(21) Appl. No.: 15/235,176

(22) Filed: Aug. 12, 2016

(65) Prior Publication Data

US 2017/0051263 A1 Feb. 23, 2017

(30) Foreign Application Priority Data

Aug. 20, 2015 (JP) ................. 2015-162962

(51) Int. Cl.
C12N 9/42 (2006.01)
C12P 19/02 (2006.01)
C12P 19/14 (2006.01)

(52) U.S. Cl.
CPC ............ *C12N 9/2437* (2013.01); *C12P 19/02* (2013.01); *C12P 19/14* (2013.01); *C12Y 302/01004* (2013.01)

(58) Field of Classification Search
None
See application file for complete search history.

(56) References Cited

U.S. PATENT DOCUMENTS

2002/0102699 A1 8/2002 Wicher et al.
2003/0054539 A1 3/2003 Schulein et al.
2009/0328259 A1* 12/2009 Harris ............... C07K 14/5431
800/298

OTHER PUBLICATIONS

Genseq Accession No. AAM50975, published May 15, 2002.*
Guo et al., "Protein tolerance to random amino acid change", Proceedings of the National Academy of Sciences USA, vol. 101, No. 25, pp. 9205-9210, 2004.*
Search Report dated Dec. 2, 2016 for European Patent Application No. 16184437.8.

(Continued)

*Primary Examiner* — Richard Ekstrom
(74) *Attorney, Agent, or Firm* — Drinker Biddle & Reath LLP

(57) ABSTRACT

A hyperthermostable endoglucanase, having an endoglucanase catalytic domain including: (A) a polypeptide including an amino acid sequence represented by SEQ ID NO: 1; (B) a polypeptide including an amino acid sequence in which at least one amino acid has been deleted, substituted, or added in the amino acid sequence represented by SEQ ID NO: 1, and having hydrolysis activity against a substrate of carboxymethyl cellulose at least under conditions of a temperature of 110° C. and a pH of 5.5; or (C) a polypeptide including an amino acid sequence having at least 55% sequence identity with the amino acid sequence represented by SEQ ID NO: 1, and having hydrolysis activity against a substrate of carboxymethyl cellulose at least under conditions of a temperature of 110° C. and a pH of 5.5.

4 Claims, 3 Drawing Sheets

(56) References Cited

OTHER PUBLICATIONS

Luisa Maurelli et al., "Evidence that the xylanase activity from Sulfolobus solfataricus Oα is encoded by the endoglucanase precursor gene(sso1354) and characterization of the associated cellulase activity", Extremophiles; Life Under Extreme Conditions, Springer-Verlag, TO, vol. 12, No. 5, Jun. 21, 2008, pp. 689-700.

* cited by examiner

FIG. 1

```
AR15G-92     1  MRAWIAVAVASLLLLLLTAAVMMKREEENKVEGMVKLSGRWDCIDVMNGEYRVCNNVWGSG   60
R. marinus   1  ------------------------------MTVELGRWDARDVAGGRVINNVWGA-      28

AR15G-92    61  EGVGRQTIEVDPFSTYFKVVETTH-SSRGVAAYPFIYKGCHWG-CTKDSGLPVKVRELRS  119
R. marinus  29  --ETAQCIEVGLETGNFTITRADHDNGNNVAAYPAIYFGCHWGACTSNSGLPRRVQELSD   86

AR15G-92   120  AHSTWIISTSGVEGTMNAAYDIWFS--VRGASSPEGGAELMIWNRGGAAPAGTKVATV    177
R. marinus  87  VRTSWTL-TPITTGRMNAAYDIWFSPVTNSGNGYSGGAELMIWLNWGGVMPGGSRVATV   145

AR15G-92   178  EVGGYVEWDVYFFKMDWNYIAYLSRRPLERV-ELDIKAFIDDALSRGYIDPEWYLDAIEAG  236
R. marinus 146  ELAGATWEVWYADWDWNYIAYRRTTPTTSVSELDLKAFIDDAVARGYIRPEWYLHAVETG   205

AR15G-92   237  FEIWRGGAGLTTLRFSAFAESNP                                       259
R. marinus 206  FELWEGGAGLRSADFSVTVQKL-                                       227
```

HYPERTHERMOSTABLE ENDOGLUCANASE

TECHNICAL FIELD

The present invention relates to a hyperthermostable endoglucanase, a polynucleotide that encodes the aforementioned hyperthermostable endoglucanase, an expression vector for expressing the aforementioned hyperthermostable endoglucanase, a transformant into which the aforementioned expression vector has been incorporated, and a method for producing a lignocellulose degradation product using the aforementioned hyperthermostable endoglucanase.

Priority is claimed on Japanese Patent Application No. 2015-162962, filed Aug. 20, 2015, the content of which is incorporated herein by reference.

SEQUENCE LISTING

The instant application contains a sequence listing which has been submitted in ASCII format via EFS-Web and is hereby incorporated by reference in its entirety. Said ASCII copy, created on Aug. 11, 2016 is named 215485_0004_ST25.txt and is 6,386 bytes in size.

BACKGROUND ART

In recent years, from the viewpoint of environmental problems such as global warming and air pollution, the development of new energy as an alternative to fossil fuel, such as photovoltaic power generation, wind power generation, and geothermal power generation is being advanced. In particular, as a means of suppressing carbon dioxide emissions, the use of plant biomass as renewable energy has been attracting attention. Plant biomass is mainly composed of cellulose, hemicellulose and lignin. Biological methods, physical methods and chemical methods are available as methods of hydrolyzing plant biomass, and biological hydrolysis methods by enzymes (cellulases) are the current mainstream. Cellulose and hemicellulose are hydrolyzed to form monosaccharides such as glucose and xylose, which can then be used as biofuels or the raw materials for chemical products.

Lignocellulose is recalcitrant due to its highly complex structure, and is difficult to degrade or hydrolyze with a single cellulolytic enzyme. Accordingly, among the various polysaccharides, hydrolysis of cellulose generally requires three types of glycoside hydrolase enzymes, namely an endoglucanase (endo-1,4-β-D-glucanase, EC 3.2.1.4), an exo-type cellobiohydrolase (1,4-β-cellobiosidase or cellobiohydrolase, EC 3.2.1.91, EC 3.2.1.176), and a β-glucosidase (EC 3.2.1.21). On the other hand, hydrolysis of hemicellulose requires a xylanase (endo-1,4-β-xylanase, EC 3.2.1.8) and a β-xylosidase (3.2.1.37).

In conventional bioethanol production using lignocellulose as a starting resource, hydrolysis processes using high solid loading (30 to 60% solid loading) have been tested with the aim of achieving a more energy-efficient conversion to ethanol. However, in this type of lignocellulose enzymatic hydrolysis using high solid loading, the viscosity of the hydrolyzed biomass solution is high, and the hydrolysis reaction of the lignocellulose tends to proceed poorly. Accordingly, by using a thermostable enzyme and performing the enzymatic hydrolysis process at a high temperature, for example 80° C. or higher, the rate of the hydrolysis reaction can be increased, and the viscosity of the hydrolyzed biomass solution can be reduced, which is expected to enable a shortening of the hydrolysis reaction time and a reduction in the amount of enzyme required. As a result, for all of the various glycoside hydrolases, the development of enzymes having superior thermal stability is very desirable.

For the purpose of lignocellulose degradation, use as a processing agent of cellulose fibers, and pulp and paper processing, numerous thermostable enzymes that can be used for lignocellulose hydrolysis treatment at a high temperature, especially endoglucanases necessary for the hydrolysis of cellulose, have been isolated to date from thermophilic bacteria, filamentous fungi, archaea and the like (for example, see Patent Document 1). In addition, attempts have also been made to further improve the specific activity and the thermal stability, for example, by using the mutants of a host organism or partially modifying the amino acid sequences of these enzymes. However, almost all of the above enzymes have optimum temperatures of 60 to 80° C., and further improvements in the thermal stability are still required. On the other hand, there are hyperthermostable endoglucanases having an optimum temperature of more than 90° C. For example, in Patent Document 2, *Rhodothermus marinus* has been reported to have an endoglucanase Cel12A with an optimum temperature of more than 105° C.

PRIOR ART LITERATURE

Patent Documents

[Patent Document 1] United States Patent Application Publication No. 2003/0054539
[Patent Document 2] United States Patent Application Publication No. 2002/0102699

SUMMARY OF THE INVENTION

Problems to be Solved by the Invention

The present invention has an object of providing a novel hyperthermostable endoglucanase which exhibits hydrolytic activity using carboxymethyl cellulose (hereinafter, may be abbreviated as CMC) as a substrate at least under conditions of a temperature of 110° C. and a pH of 5.5, a polynucleotide that encodes the aforementioned hyperthermostable endoglucanase, an expression vector for expressing the aforementioned hyperthermostable endoglucanase, a transformant into which the aforementioned expression vector has been incorporated, and a method for producing a lignocellulose degradation product using the aforementioned hyperthermostable endoglucanase.

Means for Solving the Problem

In order to achieve the above object, the inventors of the present invention extracted DNA directly from the high-temperature soils of hot springs, and by carrying out large-scale metagenomic sequencing of the microbial flora that was difficult to culture, they succeeded in obtaining a hyperthermostable endoglucanase having a novel amino acid sequence, thus enabling them to complete the present invention.

In other words, a hyperthermostable endoglucanase, a polynucleotide, an expression vector, a transformant, a method for producing a hyperthermostable endoglucanase, a glycoside hydrolase mixture, and a method for producing a lignocellulose degradation product according to the present invention have the aspects [1] to [8] described below.

[1] A hyperthermostable endoglucanase, having an endoglucanase catalytic domain including:

(A) a polypeptide including an amino acid sequence represented by SEQ ID NO: 1;

(B) a polypeptide including an amino acid sequence in which at least one amino acid has been deleted, substituted, or added in the amino acid sequence represented by SEQ ID NO: 1, and having hydrolysis activity against a substrate of carboxymethyl cellulose at least under conditions of a temperature of 110° C. and a pH of 5.5; or (C) a polypeptide including an amino acid sequence having at least 55% sequence identity with the amino acid sequence represented by SEQ ID NO: 1, and having hydrolysis activity against a substrate of carboxymethyl cellulose at least under conditions of a temperature of 110° C. and a pH of 5.5.

[2] A polynucleotide, having a region that encodes an endoglucanase catalytic domain, the region including:

(a) a nucleotide sequence that encodes a polypeptide including an amino acid sequence represented by SEQ ID NO: 1;

(b) a nucleotide sequence that encodes a polypeptide including an amino acid sequence in which at least one amino acid has been deleted, substituted, or added in the amino acid sequence represented by SEQ ID NO: 1, and having hydrolysis activity against a substrate of carboxymethyl cellulose at least under conditions of a temperature of 110° C. and a pH of 5.5;

(c) a nucleotide sequence that encodes a polypeptide including an amino acid sequence having at least 55% sequence identity with the amino acid sequence represented by SEQ ID NO: 1, and having hydrolysis activity against a substrate of carboxymethyl cellulose at least under conditions of a temperature of 110° C. and a pH of 5.5;

(d) a nucleotide sequence having at least 55% sequence identity with a nucleotide sequence represented by SEQ ID NO: 2, and encoding a polypeptide that has hydrolysis activity against a substrate of carboxymethyl cellulose at least under conditions of a temperature of 110° C. and a pH of 5.5, or (e) a nucleotide sequence of a polynucleotide which hybridizes with a polynucleotide including a nucleotide sequence represented by SEQ ID NO: 2 under a stringent condition, and being a nucleotide sequence that encodes a polypeptide having hydrolysis activity against a substrate of carboxymethyl cellulose at least under conditions of a temperature of 110° C. and a pH of 5.5.

[3] An expression vector incorporating the polynucleotide according to [2], the expression vector being capable of expressing a polypeptide having endoglucanase activity in a host cell.

[4] A transformant into which the expression vector according to [3] has been introduced.

[5] The transformant according to [4], which is a eukaryotic microbe.

[6] A method for producing a hyperthermostable endoglucanase, the method including producing a hyperthermostable endoglucanase in the transformant according to [4] or [5].

[7] A glycoside hydrolase mixture, including the hyperthermostable endoglucanase according to [1], a hyperthermostable endoglucanase encoded by the polynucleotide according to [2], or a hyperthermostable endoglucanase produced by the method for producing a hyperthermostable endoglucanase according to [6], and at least one other glycoside hydrolase.

[8] A method for producing a lignocellulose degradation product, the method including producing a lignocellulose degradation product by bringing a lignocellulose-containing material containing cellulose into contact with the hyperthermostable endoglucanase according to [1], a hyperthermostable endoglucanase encoded by the polynucleotide according to [2], the transformant according to [4] or [5], a hyperthermostable endoglucanase produced by the method for producing a hyperthermostable endoglucanase according to [6], or the glycoside hydrolase mixture according to [7].

Effects of the Invention

The hyperthermostable endoglucanase according to the present invention has hydrolysis activity against a substrate of CMC at least under conditions of a temperature of 110° C. and a pH of 5.5. For this reason, the hyperthermostable endoglucanase is suitable for a hydrolysis process of a lignocellulose-containing material containing cellulose under high temperature conditions.

Further, the polynucleotide according to the present invention, an expression vector incorporating the polynucleotide, and a transformant into which the expression vector has been introduced can be used favorably in the production of the hyperthermostable endoglucanase according to the present invention.

BRIEF DESCRIPTION OF THE DRAWINGS

FIG. 1 is an alignment diagram of the amino acid sequence (SEQ ID NO: 1) of a polypeptide (AR15G-92-6) encoded by an open reading frame AR15G-92 and the amino acid sequence (SEQ ID NO: 6) of an endoglucanase 12A (Cel12A) of *Rhodothermus marinus*.

DETAILED DESCRIPTION OF THE INVENTION

[Hyperthermostable Endoglucanase]

Figure 2:
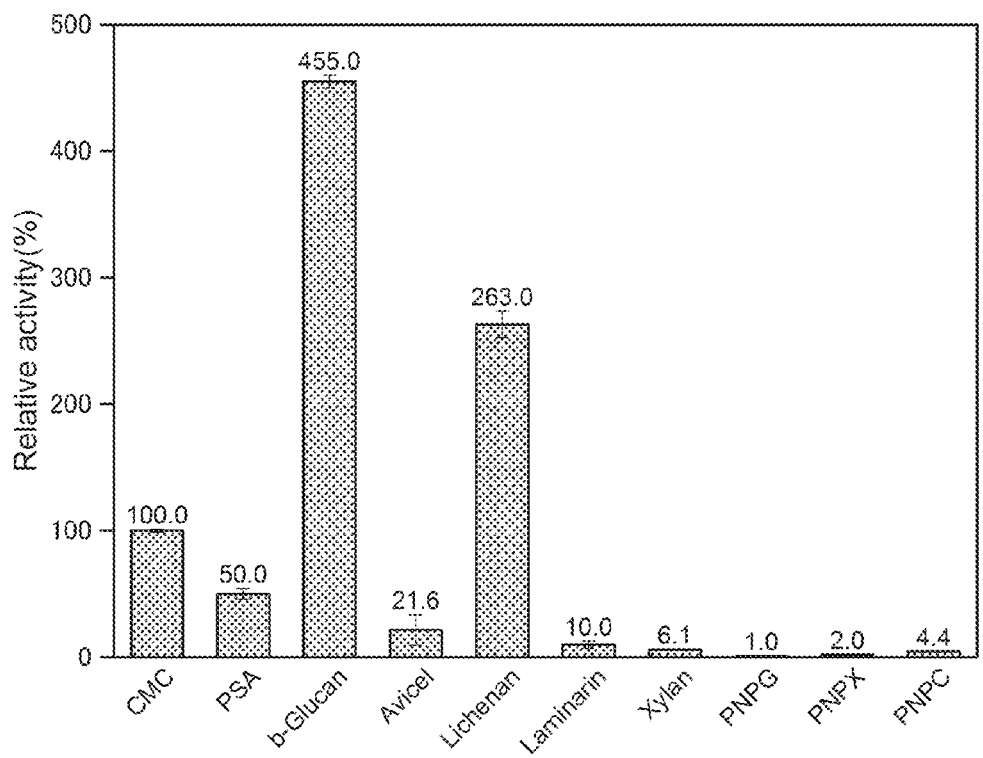
FIG. 2 is a diagram showing relative values (%) of the hydrolysis activity against various substrates of the AR15G-92-6 protein expressed in *E. coli* in Example 1.

Many microorganisms including filamentous fungi, bacteria and Archaea are difficult to culture, and it is said that about 99% of the microorganisms inhabiting microbial environments such as soil are still unknown. In particular, the culturing of microorganisms that exist in high-temperature environments is extremely difficult, and it is thought that only a mere 0.1% or less of the microorganisms that exist in soils have been able to be isolated and cultured with currently available microbial culturing techniques. This difficulty in culturing microorganisms from high-temperature soils is one of the reasons hindering the development of thermostable enzymes.

In recent years, as a result of the development of next generation giga sequencers that enable a large amount of sequencing of giga base pairs, whole genome sequencing of the microbial flora contained in soils or the like has become possible. By using this analysis technology, the metagenomic analysis method has been proposed, in which the genomic DNA of a microbial group is prepared from an environmental sample such as soil, the genomes of the group having non-uniform and miscellaneous genomic compositions are sequenced directly and comprehensively, and the sequenced data are assembled by a parallel computer, thereby reconstructing the genomic sequences of the microbial flora. This method has contributed to rapid progress in the genome sequencing of microorganisms that are difficult to culture.

As shown in Example 1 described below, the inventors of the present invention extracted the genomic DNA (metagenomic DNA) of microbial groups from collected high-temperature hot spring soils (for example, hot spring water of 58 to 78° C. containing soil, mud, biomat and biofilm and the like), and conducted shotgun sequencing and annotation of the metagenomic DNA, thus obtaining open reading frames (ORFs) encoding amino acid sequences similar to those of known endoglucanase enzymes (for example, amino acid sequences having at least 20% sequence identity, and an expectation value (E-value) of less than $1\ e^{-20}$). For each of the 106 ORFs for which an endoglucanase catalytic domain was confirmed, a primer was designed based on the nucleotide sequence information of the ORF, and gene candidates were cloned from the metagenomic DNA of the high-temperature hot spring soils by the PCR method. The PCR-cloned DNAs were incorporated into *E. coli*, and proteins encoded by these nucleotide sequences were expressed and subjected to functional screening by CMC degradation activity assay. Finally, a hyperthermostable endoglucanase having endoglucanase activity (hereinafter, may be referred to as "AR15G-92-6") was obtained from the amino acid sequences encoded by these ORFs. The amino acid sequence of AR15G-92-6 is represented by SEQ ID NO: 1, and the nucleotide sequence encoding the amino acid sequence of AR15G-92-6 is represented by SEQ ID NO: 2, respectively.

As shown in Example 1<9> described later, AR15G-92-6 exhibits hydrolysis activity against CMC, β-glucan, non-crystalline cellulose phosphoric acid swollen Avicel (hereafter often abbreviated as PSA), crystalline cellulose Avicel, and lichenan composed of β-1,3- and β-1,4-linked glucan. On the other hand, AR15G-92-6 only exhibits weak hydrolysis activity against laminarin composed of β-1,3- and β-1,6-linked glucan, xylan, and p-nitrophenyl-β-D-cellobioside ((hereafter often abbreviated as PNPC), and exhibits almost no degradation activity against p-nitrophenyl-β-D-glucopyranoside (hereafter often abbreviated as PNPG) and p-nitrophenyl-β-D-xylopyranoside (hereafter often abbreviated as PNPX).

When the amino acid sequence of AR15G-92-6 was searched against a database of known amino acid sequences, the amino acid sequence that showed the highest sequence identity was that of a known endoglucanase 12A (Cel12A) (SEQ ID NO: 6) of a thermophilic bacterium *Rhodothermus marinus*, showing the sequence identity (homology) of 53% for the GH12 (Glycoside hydrolase family 12) catalytic domain. Based on the substrate specificity and the sequence identity of the amino acid sequence with that of a known protein, it was clear that AR15G-92-6 was a novel endoglucanase belonging to the GH12 family.

AR15G-92-6 has hydrolysis activity against a substrate of CMC at least under conditions of a temperature of 110° C. and a pH of 5.5. Actually, as shown in Example 1 <10> and <11> described later, AR15G-92-6 exhibits endoglucanase activity within a broad temperature range from 60 to 130° C. and across a broad pH range of 3 to 8, exhibits strong endoglucanase activity within a temperature range from 70 to 120° C. and a pH of 3 to 8, and exhibits particularly strong endoglucanase activity within a temperature range from 90 to 110° C. and a pH of 4.5 to 6.5.

In the present description, the expression "has activity" or "exhibits activity" means that the enzyme acts against at least one substrate, with a significant difference occurring in the amount of reducing ends or the color development reaction of the hydrolyzed substrate compared with a negative control.

Accordingly, the expression "has endoglucanase activity" means that the enzyme acts at least against CMC at least under conditions of a temperature of 110° C. and a pH of 5.5, and generates a significant difference in the amount of reducing ends or the color development reaction of the hydrolyzed CMC compared with a negative control.

Generally, in a protein having some form of bioactivity, one or a plurality of amino acids can be deleted, substituted, or added, without impairing the bioactivity. In other words, in AR15G-92-6, one or a plurality of amino acids can be deleted, substituted, or added without impairing the glycoside hydrolysis activity.

Hence, the hyperthermostable endoglucanase according to the present invention is a hyperthermostable glycoside hydrolase having an endoglucanase catalytic domain including any of the following (A) to (C):

(A) a polypeptide including the amino acid sequence represented by SEQ ID NO: 1 (namely, AR15G-92-6);

(B) a polypeptide including an amino acid sequence in which at least one amino acid has been deleted, substituted, or added in the amino acid sequence represented by SEQ ID NO: 1, and having hydrolysis activity against a substrate of CMC at least under conditions of a temperature of 110° C. and a pH of 5.5; or (C) a polypeptide including an amino acid sequence having at least 55% sequence identity with the amino acid sequence represented by SEQ ID NO: 1, and having hydrolysis activity against a substrate of CMC at least under conditions of a temperature of 110° C. and a pH of 5.5.

In the present description, a "polypeptide in which an amino acid is deleted" means a polypeptide in which a portion of the amino acids which constitute the polypeptide is missing (removed).

In the present description, a "polypeptide in which an amino acid is substituted" means a polypeptide in which an amino acid which constitutes the polypeptide has been replaced with a different amino acid.

In the present description, a "polypeptide in which an amino acid is added" means a polypeptide in which a new amino acid has been inserted within the polypeptide.

In the above polypeptide of (B), the number of amino acids deleted, substituted, or added in the amino acid sequence represented by SEQ ID NO: 1 is preferably 1 to 20, more preferably 1 to 10, and still more preferably 1 to 5. The position of the amino acids deleted, substituted, or added in the amino acid sequence is not particularly limited as long as the polypeptide including the amino acid sequence subjected to modification such as deletion has endoglucanase activity.

In the above polypeptide of (C), the sequence identity with the amino acid sequence represented by SEQ ID NO: 1 is not specifically limited as long as it is 55% or greater but less than 100%, but the sequence identity is preferably 75% or greater but less than 100%, more preferably 80% or greater but less than 100%, still more preferably 85% or greater but less than 100%, still more preferably 90% or greater but less than 100%, and most preferably 95% or greater but less than 100%.

The sequence identity (homology) between a pair of amino acid sequences is determined by juxtaposing the two amino acid sequences, while inserting gaps in some parts of the sequences to account for insertions and deletions, so as to achieve the best match between corresponding amino acids, and then calculating the proportion of matched amino acids relative to the whole amino acid sequences, excluding gaps, in the resulting alignment. The sequence identity between a pair of amino acid sequences can be determined using a variety of homology search software well known in the art. The sequence identity value between amino acid sequences in the present invention is obtained by calculation on the basis of an alignment obtained from the publicly known homology search software BLASTP.

The aforementioned polypeptides of (B) and (C) may be artificially designed, or may be homologues of AR15G-92-6 or the like, or partial proteins thereof.

Each of the aforementioned polypeptides of (A) to (C) may be chemically synthesized based on the amino acid sequence, or may be generated by a protein expression system using the polynucleotide according to the present invention described below. Further, each of the polypeptides of (B) and (C) can also be artificially synthesized based on the polypeptide including the amino acid sequence represented by SEQ ID NO: 1, by using a gene recombination technique to introduce amino acid mutation(s).

Each of the polypeptides of (A) to (C) has hydrolysis activity against a substrate of CMC at least under conditions of a temperature of 110° C. and a pH of 5.5. As a result, a hyperthermostable endoglucanase can be obtained by having any of the polypeptides of (A) to (C) as the endoglucanase catalytic domain.

The hyperthermostable endoglucanase according to the present invention uses, as a substrate, at least one compound selected from the group consisting of a compound having β-1,3 and β-1,4 linkages and a compound having β-1,4 linkages.

Examples of the compounds composed of β-1,3 and β-1,4 linkages include lichenan, β-glucan, and the like. Examples of the compounds composed of β-1,4 linkages include crystalline celluloses such as Avicel, crystalline bacterial cellulose (bacterial microcrystalline cellulose, hereafter sometimes abbreviated as BMCC) and filter paper, CMC, PSA, cellobiose, and the like.

The hyperthermostable endoglucanase according to the present invention preferably uses, as a substrate, at least one compound selected from the group consisting of a compound composed of β-1,3 and β-1,6 linkages, such as laminarin, and xylan, in addition to the compound composed of β-1,3 and β-1,4 linkages and the compound composed of β-1,4 linkages.

In addition to the above substrates, the hyperthermostable endoglucanase according to the present invention may also use other glucans or the like as a substrate. Examples of substrates that can act as substrates for the hyperthermostable endoglucanase according to the present invention include PNPX, PNPG, p-nitrophenyl-α-L-arabinofuranoside, p-nitrophenyl-α-L-arabinopyranoside, p-nitrophenyl-β-L-arabinopyranoside, p-nitrophenyl-β-D-mannopyranoside, p-nitrophenyl-α-D-galactopyranoside, p-nitrophenyl-β-D-galactopyranoside; glucans composed of β-1,3 linkages; and oligosaccharides composed of β-1,6 linkages such as gentiobiose.

The hyperthermostable endoglucanase according to the present invention preferably exhibits CMC hydrolysis activity at least under conditions of a pH of 5.5 and within a temperature range from 90 to 115° C., more preferably within a temperature range from 70 to 120° C., and still more preferably within a wide temperature range from 60 to 130° C. The optimum temperature for the CMC hydrolysis activity of the hyperthermostable endoglucanase according to the present invention is preferably within a range from 100 to 115° C. under a condition of a pH of 5.5.

The term "thermostable" used in relation to the thermostable endoglucanase according to the present invention means the endoglucanase has endoglucanase activity within a temperature range from 60 to 130° C.

The optimum pH for the endoglucanase activity of the hyperthermostable endoglucanase according to the present invention varies depending on the reaction temperature and the substrate, but falls within a range from pH 5.0 to 6.0. For example, the optimum pH at 95° C. in the case of using CMC as a substrate is 5.5. The hyperthermostable endoglucanase according to the present invention preferably exhibits endoglucanase activity at least within a range from pH 4.5 to 6.5, and more preferably exhibits endoglucanase activity within a range from pH 3 to 8.

In addition to the endoglucanase activity, the hyperthermostable endoglucanase according to the present invention preferably further exhibits xylanase activity at least under conditions of a temperature of 99° C. and a pH of 5.5, more preferably within ranges from 90 to 110° C. and from pH 4.5 to 6.5, and still more preferably within ranges from 60 to 130° C. and from pH 3 to 8.

In addition to the endoglucanase activity and xylanase activity, the hyperthermostable endoglucanase according to the present invention may also have other glycoside hydrolase activity besides the endoglucanase activity and xylanase activity. Examples of this other glycoside hydrolase activity include β-xylosidase activity, β-glucosidase activity and cellobiohydrolase activity.

The hyperthermostable endoglucanase according to the present invention may be an enzyme composed solely of the endoglucanase catalytic domain including any of the aforementioned polypeptides of (A) to (C), or may also include other domains. Examples of these other domains include other domains of conventionally known glycoside hydrolases besides the enzyme catalytic domain. For example, the hyperthermostable endoglucanase according to the present invention also includes enzymes obtained by substituting an enzyme catalytic domain in a publicly known glycoside hydrolase with any of the aforementioned polypeptides of (A) to (C).

When the hyperthermostable endoglucanase according to the present invention includes one or more other domains besides the endoglucanase catalytic domain, it is also preferable that the thermostable endoglucanase includes a cellulose-binding module. The cellulose-binding module may be positioned upstream (on the N-terminal side) or downstream (on the C-terminal side) of the endoglucanase catalytic domain. Further, the cellulose-binding module and the endoglucanase catalytic domain may be either bonded directly or bonded via a linker region of appropriate length. In the hyperthermostable endoglucanase according to the present invention, a cellulose-binding module preferably exists either upstream or downstream from the endoglucanase catalytic domain with a linker region positioned therebetween, and a hyperthermostable endoglucanase in which a cellulose-binding module exists upstream of the endoglucanase catalytic domain with a linker region positioned therebetween is particularly preferred.

The cellulose-binding module included in the hyperthermostable endoglucanase according to the present invention is a region having the ability to bind cellulose, such as the ability to bind PSA or crystalline Avicel, and there are no particular limitations on the amino acid sequence of the module. Examples of the aforementioned cellulose-binding module include the types of cellulose-binding modules present in known proteins, and appropriately modified versions thereof. Further, in those cases where the hyperthermostable endoglucanase according to the present invention includes both the endoglucanase catalytic domain and a cellulose-binding module, it is preferable that these are bonded via a linker sequence. There are no particular limitations on the amino acid sequence or the length and the like of the linker sequence.

The hyperthermostable endoglucanase according to the present invention may also have, at either the N-terminal or the C-terminal, a signal peptide capable of migration to and localization within a specific region within a cell, or a signal peptide that causes secretion from a cell. Examples of these types of signal peptides include apoplastic transport signal peptides, endoplasmic reticulum retention signal peptides, nuclear transport signal peptides, and secretory signal peptides. Specific examples of the endoplasmic reticulum retention signal peptides include signal peptides including an HDEL amino acid sequence. In those cases where the hyperthermostable endoglucanase according to the present invention has a signal peptide at the N-terminal or the C-terminal, the hyperthermostable endoglucanase expressed in a transformant can be secreted from the cell or localized within the endoplasmic reticulum or the like of the cells.

Furthermore, the hyperthermostable endoglucanase according to the present invention may also have various types of tags added, for example at the N-terminal or the C-terminal of the hyperthermostable endoglucanase, so as to facilitate easy purification in the case of generation using an expression system. Examples of tags that may be used include the types of tags widely used in the expression or purification of recombinant proteins, such as His tags, HA (hemagglutinin) tags, Myc tags and Flag tags.

In other words, one aspect of the hyperthermostable endoglucanase according to the present invention contains a endoglucanase catalytic domain including any of the aforementioned polypeptides of (A) to (C); and also contains, according to need, at least one moiety selected from the group consisting of a cellulose-binding module positioned either upstream (on the N-terminal side) or downstream (on the C-terminal side) of the endoglucanase catalytic domain, a linker region, a signal peptide added to either the N-terminal or the C-terminal, and a tag added to either the N-terminal or the C-terminal.

[Polynucleotide Encoding Hyperthermostable Endoglucanase]

The polynucleotide according to the present invention encodes the hyperthermostable endoglucanase according to the present invention. The hyperthermostable endoglucanase can be produced by using the expression system of a host made by introducing an expression vector incorporating the polynucleotide into the host.

Specifically, the polynucleotide according to the present invention is a polynucleotide having a region encoding an endoglucanase catalytic domain, the region including any of the following nucleotide sequences (a) to (e):

(a) a nucleotide sequence encoding a polypeptide including the amino acid sequence represented by SEQ ID NO: 1, (b) a nucleotide sequence that encodes a polypeptide including an amino acid sequence in which at least one amino acid has been deleted, substituted, or added in the amino acid sequence represented by SEQ ID NO: 1, and having hydrolysis activity against a substrate of CMC at least under conditions of a temperature of 110° C. and a pH of 5.5, (c) a nucleotide sequence that encodes a polypeptide including an amino acid sequence having at least 55% sequence identity with the amino acid sequence represented by SEQ ID NO: 1, and having hydrolysis activity against a substrate of CMC at least under conditions of a temperature of 110° C. and a pH of 5.5, (d) a nucleotide sequence having at least 55% sequence identity with a nucleotide sequence represented by SEQ ID NO: 2, and encoding a polypeptide that has hydrolysis activity against a substrate of CMC at least under conditions of a temperature of 110° C. and a pH of 5.5: or (e) a nucleotide sequence of a polynucleotide which hybridizes with a polynucleotide including a nucleotide sequence represented by SEQ ID NO: 2 under a stringent condition, and being a nucleotide sequence that encodes a polypeptide having hydrolysis activity against a substrate of CMC at least under conditions of a temperature of 110° C. and a pH of 5.5.

In the present description, a "polynucleotide in which a nucleotide is deleted" means a polynucleotide in which a portion of the nucleotides which constitute the polynucleotide is missing (removed).

In the present description, a "polynucleotide in which a nucleotide is substituted" means a polynucleotide in which a nucleotide which constitutes the polynucleotide has been replaced with a different nucleotide.

In the present description, a "polynucleotide in which a nucleotide is added" means a polynucleotide in which a new nucleotide has been inserted within the polynucleotide.

In the present description, the expression "stringent conditions" can be exemplified by the method disclosed in Molecular Cloning: A Laboratory Manual, Third Edition (Sambrook et al., Cold Spring Harbor Laboratory Press). This example includes conditions in which hybridization is performed by incubation in a hybridization buffer composed of 6×SSC (composition of 20×SSC: 3 M sodium chloride, 0.3 M citric acid solution, pH 7.0), 5×Denhardt's solution (composition of 100×Denhardt's solution: 2% by mass of bovine serum albumin, 2% by mass of Ficoll, 2% by mass of polyvinylpyrrolidone), 0.5% by mass of SDS, 0.1 mg/mL of salmon sperm DNA, and 50% formamide, at a temperature of 42 to 70° C. for several hours to overnight. The washing buffer used in the washing performed after the incubation is preferably 1×SSC solution containing 0.1% by mass of SDS, and is more preferably 0.1×SSC solution containing 0.1% by mass of SDS.

In the aforementioned nucleotide sequences of (a) to (e), it is preferable to select a degenerate codon having a high frequency of usage in the host. For example, the aforementioned nucleotide sequence of (a) may be either the nucleotide sequence represented by SEQ ID NO: 2, or a nucleotide sequence obtained by modifying the nucleotide sequence represented by SEQ ID NO: 2 to codons having a higher frequency of usage in the host without changing the amino acid sequence encoded by the nucleotide sequence. This modification of codons can be achieved using a known gene sequence variation technique or artificial gene synthesis.

The polynucleotide including the nucleotide sequence represented by SEQ ID NO: 2 may be chemically synthesized based on the nucleotide sequence information, or may be obtained from the natural world by using gene recombination techniques as either a full length gene that encodes AR15G-92-6 (also referred to as the "AR15G-92-6 gene" or the "gene clone AR15G-92-6") or a partial region thereof including the endoglucanase catalytic domain (in the case of the AR15G-92-6 gene, a region encoding the partial region including the 150 amino acid residues from the aspartic acid (D) at position 107 through to the glutamic acid (E) at position 256 in SEQ ID NO: 1). The full length of the AR15G-92-6 gene or the partial region thereof can be obtained, for example, by collecting a sample containing microorganisms from the natural world, and conducting PCR using a genomic DNA recovered from the sample as a template, with a forward primer and a reverse primer designed by normal methods based on the nucleotide sequence represented by SEQ ID NO: 2. The cDNA synthesized by a reverse transcription reaction using mRNA recovered from the sample as a template may also be used as a template. The sample from which the nucleic acid for use as a template is recovered is preferably a sample collected from a high-temperature environment such as hot spring soil.

In the aforementioned nucleotide sequence of (d), the sequence identity with the nucleotide sequence represented by SEQ ID NO: 2 is not specifically limited as long as it is 55% or greater but less than 100%, but the sequence identity is preferably 75% or greater but less than 100%, more preferably 80% or greater but less than 100%, still more preferably 85% or greater but less than 100%, still more preferably 90% or greater but less than 100%, and most preferably 95% or greater but less than 100%.

The sequence identity (homology) between a pair of nucleotide sequences is determined by juxtaposing the two nucleotide sequences, while inserting gaps in some parts of the sequences to account for insertions and deletions, so as to achieve the best match between corresponding nucleotides, and then calculating the proportion of matched nucleotides relative to the whole nucleotide sequences, excluding gaps, in the resulting alignment. The sequence identity between a pair of nucleotide sequences can be determined using a variety of homology search software well known in the art. The sequence identity value between nucleotide sequences in the present invention is obtained by calculation on the basis of an alignment obtained from the publicly known homology search software BLASTN.

For example, each of the polynucleotides including the aforementioned nucleotide sequence of (b), (c) or (d) can be artificially synthesized by deleting, substituting, or adding one or a plurality of nucleotides in a polynucleotide including the nucleotide sequence represented by SEQ ID NO: 2. Further, the nucleotide sequence of (b), (c) or (d) may also be a full length sequence of a homologous gene of the AR15G-92-6 gene or a partial sequence thereof. The homologous gene of the AR15G-92-6 gene can be obtained by a gene recombination technique used in obtaining homologous genes of a gene for which the nucleotide sequence is already known.

The polynucleotide according to the present invention may have only the region encoding the endoglucanase catalytic domain, or may also have, in addition to this region, one or more other regions encoding a cellulose-binding module, a linker sequence, various types of signal peptides, or various types of tags or the like.

In other words, one aspect of the polynucleotide according to the present invention contains a region encoding an endoglucanase catalytic domain, the region including one of the aforementioned nucleotide sequences of (a) to (e), and also contains, according to need, a region encoding at least one moiety selected from the group consisting of a cellulose-binding module, a linker region, a signal peptide and a tag.

[Expression Vector]

The expression vector according to the present invention incorporates the aforementioned polynucleotide according to the present invention, and is capable of expressing, in a host cell, a polypeptide having hydrolysis activity against a substrate of CMC at least under conditions of a temperature of 110° C. and a pH of 5.5. In other words, the expression vector of the present invention is an expression vector into which the polynucleotide according to the present invention has been incorporated in a state capable of expressing the hyperthermostable endoglucanase according to the present invention. More specifically, it is necessary that an expression cassette, composed, in order from the upstream side, of DNA having a promoter sequence, the aforementioned polynucleotide according to the present invention and DNA having a terminator sequence, is incorporated into the expression vector. Incorporation of the polynucleotide into an expression vector can be achieved using known gene recombination techniques. A commercially available expression vector preparation kit may also be used to achieve incorporation of the polynucleotide into the expression vector.

In the present description, an "expression vector" is a vector including, in order from the upstream side, DNA having a promoter sequence, DNA having a sequence for incorporating foreign DNA, and DNA having a terminator sequence.

The aforementioned expression vector may be a vector for introduction into a prokaryotic cell such as *E. coli*, or a vector for introduction into a eukaryotic cell such as a yeast, a filamentous fungus, an insect cultured cell, a mammalian cultured cell, or a plant cell. Any arbitrary widely used expression vector can be selected and used in accordance with the respective host.

The expression vector according to the present invention is preferably an expression vector into which not only the aforementioned polynucleotide according to the present invention, but also a drug resistance gene or the like, has been incorporated. This facilitates the screening of host cells transformed by the expression vector and non-transformed host cells.

Examples of the drug resistance gene include a kanamycin resistance gene, a hygromycin resistance gene and a bialaphos resistance gene.

[Transformant]

The transformant according to the present invention is a transformant into which the expression vector according to the present invention has been introduced. In this transformant, the hyperthermostable endoglucanase according to the present invention can be expressed. The host into which the expression vector is introduced may be a prokaryotic cell such as *E. coli*, or a eukaryotic cell such as a yeast, a filamentous fungus, an insect cultured cell, a mammalian cultured cell, or a plant cell. In other words, examples of the transformant according to the present invention include *E. coli*, a yeast, a filamentous fungus, an insect cultured cell, a mammalian cultured cell or a plant cell into which the expression vector according to the present invention has been introduced.

By culturing a transformant of *E. coli*, the hyperthermostable endoglucanase according to the present invention can be generated more easily and in large amounts. On the other hand, because proteins are glycosylated in eukaryotic cells, by using a transformant of a eukaryotic cell, a hyperthermostable endoglucanase can be generated which exhibits superior thermal stability to that achieved by using a transformant of a prokaryotic cell.

There are no particular limitations on the method used for producing the transformant using the expression vector, and the types of methods typically used in the production of transformants can be employed. Examples of methods that can be used include a heat shock method, an *Agrobacterium* method, a particle gun method, an electroporation method, and a PEG (polyethylene glycol) method. Of these, if the host is a plant cell, a particle gun method or an *Agrobacterium* method is preferred.

When a prokaryotic cell, a yeast, a filamentous fungus, an insect cultured cell, or a mammalian cultured cell or the like is used as the host, the obtained transformant can generally be cultured by a conventional method in a similar manner to that of the non-transformed host.

[Method for Producing Hyperthermostable Endoglucanase]

The method for producing a hyperthermostable endoglucanase according to the present invention is a method for generating a hyperthermostable endoglucanase in the aforementioned transformant according to the present invention. By culturing a transformant that has been produced using an expression vector into which the aforementioned polynucleotide according to the present invention has been incorporated downstream from a promoter having no ability to regulate the timing or the like of the expression, the hyperthermostable endoglucanase according to the present invention can be expressed constitutively within the transformant. On the other hand, in the case of a transformant produced using a so-called expression inducible promoter to induce the expression by means of a specific compound or temperature condition or the like, the hyperthermostable endoglucanase according to the present invention can be expressed in the transformant by conducting an induction treatment suitable for the respective expression-inducing condition.

The hyperthermostable endoglucanase generated by the transformant may be used in a state where it is retained inside the transformant, or may be extracted from the transformant and purified.

The method used for extracting and purifying the hyperthermostable endoglucanase according to the present invention from the transformant is not particularly limited, as long as the method does not impair the glycoside hydrolysis activity of the hyperthermostable endoglucanase, and extraction can be carried out by methods commonly used for extracting polypeptides from cells or biological tissue. Examples of the method include a method in which the transformant is immersed in an appropriate extraction buffer to extract the hyperthermostable endoglucanase, and the resulting liquid extract and the solid residue are then separated. The extraction buffer preferably contains a solubilizing agent such as a surfactant. If the transformant is a plant, then the transformant may be shredded or crushed prior to immersion in the extraction buffer. Further, in terms of the method used for separating the liquid extract and the solid residue, known solid-liquid separation treatments such as a filtration method, pressurized filtration method or centrifugation treatment may be used, or the extraction buffer containing the immersed transformant may be squeezed. The hyperthermostable endoglucanase in the liquid extract can be purified by known purification methods such as a salting-out method, ultrafiltration method, or chromatography method.

If the hyperthermostable endoglucanase according to the present invention is expressed in a state having a secretory signal peptide in the transformant, then a solution containing the hyperthermostable endoglucanase can be readily obtained by culturing the transformant and then collecting the culture liquid supernatant obtained by removal of the transformant from the obtained culture. Further, if the hyperthermostable endoglucanase according to the present invention has a tag such as a His tag, then the hyperthermostable endoglucanase in the liquid extract or in the culture supernatant can be easily purified by an affinity chromatography method using the tag.

In other words, the method for producing a hyperthermostable endoglucanase according to the present invention includes generating the hyperthermostable endoglucanase within the transformant according to the present invention, and also includes, according to need, extracting the hyperthermostable endoglucanase from the transformant and purifying the hyperthermostable endoglucanase.

[Glycoside Hydrolase Mixture]

The glycoside hydrolase mixture according to the present invention includes the aforementioned hyperthermostable endoglucanase according to the present invention or a hyperthermostable endoglucanase produced by the method for producing a hyperthermostable endoglucanase according to the present invention, and at least one other glycoside hydrolase. The hyperthermostable endoglucanase produced by the aforementioned method for producing a hyperthermostable endoglucanase according to the present invention may be in a state where it is retained inside the transformant, or may be extracted from the transformant and purified. By using the hyperthermostable endoglucanase according to the present invention as a mixture with one or more other glycoside hydrolases in a polysaccharide hydrolysis reaction, materials composed of lignocellulose containing persistent cellulose can be degraded more efficiently.

There are no particular limitations on the other glycoside hydrolase besides the aforementioned hyperthermostable endoglucanase included in the glycoside hydrolase mixture, as long as it exhibits lignocellulose hydrolysis activity. Examples of the other glycoside hydrolase besides the aforementioned hyperthermostable endoglucanase included in the glycoside hydrolase mixture include hemicellulases such as xylanases and β-xylosidases, as well as cellobiohydrolases, β-glucosidases and endoglucanases. The glycoside hydrolase mixture according to the present invention is preferably a mixture containing at least one glycoside hydrolase selected from among hemicellulases and endoglucanases in addition to the aforementioned hyperthermostable endoglucanase, and is more preferably a mixture containing both a hemicellulase and an endoglucanase in addition to the aforementioned hyperthermostable endoglucanase. Among the various possibilities, the glycoside hydrolase mixture according to the present invention is preferably a mixture containing at least one glycoside hydrolase selected from the group consisting of xylanases, β-xylosidases, cellobiohydrolases and β-glucosidases in addition to the aforementioned hyperthermostable endoglucanase, and is more preferably a mixture containing all of a xylanase, a β-xylosidase, a cellobiohydrolase and a β-glucosidase in addition to the hyperthermostable endoglucanase.

The other glycoside hydrolase included in the glycoside hydrolase mixture is preferably a thermostable glycoside hydrolase having glycoside hydrolase activity at least at 110° C., and is more preferably a thermostable glycoside hydrolase having glycoside hydrolase activity at 60 to 130° C. By ensuring that all of the enzymes contained in the glycoside hydrolase mixture are thermostable (that is, have an optimum temperature for the enzymatic activity or a thermal denaturation temperature for the enzyme protein of 60° C. or higher), the lignocellulose degradation reaction by the glycoside hydrolase mixture can be conducted efficiently under high-temperature conditions. In other words, if the glycoside hydrolase mixture contains only thermostable glycoside hydrolases, then by using the glycoside hydrolase mixture in a hydrolysis treatment of a material composed of lignocellulose containing cellulose, it becomes possible to conduct the lignocellulose hydrolysis reaction in a high-temperature environment in which the hydrolysis temperature is from 60 to 130° C. (namely, a high-temperature hydrolysis). With this high-temperature hydrolysis, the amount of enzymes and the time required for the hydrolysis can be reduced markedly, and the hydrolysis costs can be cut dramatically.

[Method for Producing Lignocellulose Degradation Product]

The method for producing a lignocellulose degradation product according to the present invention is a method for obtaining a lignocellulose degradation product by hydrolyzing a material composed of lignocellulose containing cellulose with the hyperthermostable endoglucanase according to the present invention to produce oligosaccharides. More specifically, a material composed of lignocellulose containing hemicellulose or cellulose is brought into contact with the hyperthermostable endoglucanase according to the present invention, the transformant according to the present invention, a hyperthermostable endoglucanase produced by the method for producing a hyperthermostable endoglucanase according to the present invention, or the glycoside hydrolase mixture according to the present invention, thereby producing a lignocellulose degradation product containing the degradation product of the aforementioned hemicellulose or cellulose.

It should be noted that, more specifically, the term "degradation product of hemicellulose or cellulose" used herein refers to the product generated as a result of the cleavage of the glycosidic bond of hemicellulose or cellulose.

The material composed of lignocellulose containing hemicellulose or cellulose is not particularly limited as long as it contains hemicellulose or cellulose. Specific examples of the material include cellulosic biomass such as weeds and agricultural waste materials, or used paper or the like. The material is preferably subjected to a mechanical treatment such as crushing or shredding, a chemical treatment with acid or alkali or the like, or a treatment such as immersion or dissolution in an appropriate buffer, prior to being brought into contact with the hyperthermostable endoglucanase according to the present invention.

The reaction conditions for the hydrolysis reaction of the material composed of lignocellulose containing hemicellulose or cellulose by the hyperthermostable endoglucanase according to the present invention may be any conditions under which the hyperthermostable endoglucanase exhibits endoglucanase activity, and the conditions under which the hyperthermostable endoglucanase exhibits endoglucanase activity and xylanase activity are preferred. For example, the reaction is preferably conducted at a temperature of 60 to 130° C. and a pH of 3 to 8, more preferably conducted at a temperature of 70 to 120° C. and a pH of 4.0 to 7.5, and still more preferably conducted at a temperature of 90 to 115° C. and a pH of 5.0 to 7.0. The reaction time for the hydrolysis reaction may be adjusted appropriately with due consideration of the type, the method of pretreatment, and the amount and the like of the above material supplied to the hydrolysis reaction. For example, the hydrolysis reaction may be performed for a reaction time of 10 minutes to 100 hours, but in the case of degradation of a cellulosic biomass, the hydrolysis reaction is typically performed for a reaction time of 1 to 100 hours.

In the hydrolysis reaction of the material composed of lignocellulose containing hemicellulose or cellulose, it is also preferable to use at least one other type of glycoside hydrolases in addition to the hyperthermostable endoglucanase according to the present invention. This other glycoside hydrolase may be similar to the glycoside hydrolases mentioned above for inclusion in the aforementioned glycoside hydrolase mixture, and is preferably a thermostable glycoside hydrolase having glycoside hydrolase activity at least at 110° C., and preferably at least at temperatures of 60 to 130° C. Further, one aspect of the aforementioned method for producing a lignocellulose degradation product uses the hyperthermostable endoglucanase according to the present invention, the transformant according to the present invention, or a hyperthermostable endoglucanase produced by the method for producing a hyperthermostable endoglucanase according to the present invention, whereas another aspect of the method uses the aforementioned glycoside hydrolase mixture.

EXAMPLES

Next, the present invention is described in further detail based on a series of Examples, but the present invention is in no way limited by the following Examples.

[Example 1] Cloning of Novel Hyperthermostable Endoglucanase from Hot Spring Soil <1> DNA Extraction from Hot Spring Soil and Whole Genome Sequencing (WGS)

With the purpose of searching for genes of hyperthermostable endoglucanase, soil DNA was collected from neutral to weakly alkaline hot springs, and nucleotide sequencing was conducted of the metagenomic DNA of the microbial flora contained in the soils.

The soil samples from neutral to weakly alkaline hot springs were obtained by collecting hot spring water containing soil, clay and biomat from five sampling points (metagenomic DNA samples N2, AR19, AR15, OJ1 and H1) at 3 locations in Japan having gushing high-temperature outdoor hot springs. These hot spring soil samples each had a temperature within a range from 58 to 78° C. and a pH within a range from 7.2 to 8 at the time of collection.

DNA was extracted from 10 g of each of the collected hot spring soil samples by using a DNA extraction kit (ISOIL Large for Beads ver. 2, manufactured by Nippon Gene Co., Ltd.). 5 µg of the extracted DNA was subjected to shotgun sequencing of the metagenomic DNA by using the sequencer GS FLX Titanium 454 manufactured by Roche Diagnostics K.K. The remaining DNA was used for PCR cloning of the endoglucanase gene.

Metagenomic DNA sequencing of the hot spring soil sample AR15 yielded a whole genome sequence (WGS) data set having an average read length of 370 bp, a total read number of 5,419,406, and a total quantity of sequenced genomes of 2,007,725,040 bp.

<2> Assembly and Statistics of Hot Spring Metagenomic Data

For the nucleotide sequences read by the 454 sequencer, the output from the Roche 454 (sff file) was subjected to a second base calling using Pyrobayes (Quinlan et al., Nature Methods, 2008, vol. 5, pp. 179 to 181), and a FASTA format sequence file and quality value file were obtained. Ends were cut from the obtained sequence reads to improve quality, and the reads were assembled using the 454 Life Sciences assembly software Newbler version 2.3. Assembly was performed under settings including "minimum acceptable overlap match (mi)=0.9", "option: -large (for large or complex genomes, speeds up assembly but reduces accuracy)".

The total contig length of all contigs assembled to at least 100 bp totaled 118,600,846 bp, and this data set was used for cellulase gene analysis. Of the total read length of 5,419,406 reads, 4,805,640 reads were assembled into contigs having an average of at least 1,146 bp (a total of 103,508 contigs), of which the maximum contig length was 151,585 bp.

<3> Prediction of Open Reading Frames (ORFs) of Endoglucanase

Sequences having EC numbers of 3.2.1.4 (cellulase), 3.2.1.21 (β-glucosidase), 3.2.1.37 (β-xylosidase), 3.2.1.91 (cellulose 1,4-β-cellobiosidase) and 3.2.1.8 (endo-1,4-β-xylanase) were downloaded (date of access: 2011 Dec. 9) from the UniProt database (http://www.uniprot.org/), and a proteome local database of these glycoside hydrolase genes was constructed. The annotation software Orphelia (Hoff et al., Nucleic Acids Research, 2009, 37 (Web Server issue: W101 to W105) was used to predict a gene region (=open reading frame, sometimes abbreviated as ORF) from the contig sequences obtained in the above section <2> (Orphelia option: default (model=Net 700, maxoverlap=60)). In order to extract glycoside hydrolase genes from the predicted ORFs, reference was made to the local database using BLASTP (blastall ver. 2.2.18). The optional conditions for BLASTP were set such that: "Filter query sequence=false", "Expectation value (E)<1e$^{-20}$" (hereafter, default values were set such that: "Cost to open a gap=-1", "Cost to extended gap=-1", "X dropoff value for gapped alignment=0", "Threshold for extending hits=0", and "Word size=default"), and the hit ORF sequences were collected as the nucleotide sequences of glycoside hydrolase genes. The collected nucleotide sequences included the genes of various glycoside hydrolases such as cellulases, endohemicellulases, and debranching enzymes.

<4> Glycoside Hydrolase (GH) Family Classification of Genes

Functional classification of the nucleotide sequences collected in section <3> above was performed with reference to the protein functional domain sequence database Pfam HMMs (Pfam version 23.0 and HMMER v2.3; Finn et al., Nucleic Acids Research Database, 2010, Issue 38, pp. D211-222). Specifically, the glycoside hydrolase (GH) family of each of the nucleotide sequences collected in section <3> above was determined on the basis of homology with the Pfam domain database by using the protein motif search program HMMER (Durbin et al., "The theory behind profile HMMs. Biological sequence analysis: probabilistic models of proteins and nucleic acids", 1998, Cambridge University Press; hmmpfam (Ver. 2.3.2), E-value cutoff<1e$^{-5}$); Database=Pfam_fs (models that can be used to find fragments of the represented domains in a sequence)). Nucleotide sequences which covered 70% or more of the GH catalytic domain sequence were counted as enzyme genes belonging to that particular family.

Based on the BLASTP homology search using the metagenome AR15 sequence data, 106 ORFs were predicted as endoglucanase genes. The GH family classifications of these 106 ORFs are shown in Table 1. As shown in Table 1, 13 full-length ORFs of endoglucanase genes belonging to the GH family 5, 4 full-length ORFs of endoglucanase genes belonging to the GH family 9, and 4 full-length ORFs of endoglucanase genes belonging to the GH family 12 were obtained from the metagenome AR15. Primers were designed for all of these full-length ORFs that were predicted as endoglucanase genes, and these genes were cloned from the hot spring soil metagenomic DNA by PCR. As a result, an endoglucanase gene was isolated from the ORF AR15G-92 belonging to the GH family 12 and having an endoglucanase gene sequence.

TABLE 1

|  | GH5 | GH9 | GH12 | GH48 | Other GH families | Total |
| --- | --- | --- | --- | --- | --- | --- |
| Full-length ORFs | 13 | 4 | 4 | 0 | 40 | 61 |
| Incomplete ORFs | 3 | 3 | 1 | 1 | 37 | 45 |
| Total | 16 | 7 | 5 | 1 | 77 | 106 |

<5> Open Reading Frame AR15G-92

The open reading frame AR15G-92 (SEQ ID NO: 2) encoded a polypeptide (SEQ ID NO: 1) including 259 amino acid residues and was a full-length sequence, such that the polypeptide started from methionine (M) which was an amino acid residue at position 1 corresponding to an initiation codon, and the 3' end of the nucleotide sequence encoding the polypeptide ended with a termination codon. According to analysis using the signal sequence prediction software SignalP 4.1, the 24 amino acid residues from the methionine (M) at position 1 through to the arginine (R) at position 24 function as a secretion signal in the polypeptide encoded by the open reading frame AR15G-92. Further, based on the sequence homology of the motif, it was presumed that the 150 amino acid residues from the aspartic acid (D) at position 107 through to the glutamic acid (E) at position 256 in the polypeptide encoded by the open reading frame AR15G-92 encoded the GH12 catalytic domain. The known amino acid sequence that showed the highest sequence identity with the amino acid sequence encoded by the above ORF was that of an endoglucanase 12A (Cel12A) (PDB: 2BW8_A) of a thermophilic bacterium *Rhodothermus marinus*. Since the sequence homology value between the two amino acid sequences that was calculated by the ClustalW algorithm was 53% for the GH12 catalytic domain, the above ORF was verified to have a novel sequence.

FIG. 1 shows an alignment of the amino acid sequence (SEQ ID NO: 1) of a polypeptide encoded by the open reading frame AR15G-92 and the amino acid sequence (SEQ ID NO: 6) of Cel12A of *Rhodothermus marinus*. In FIG. 1, the amino acids shown in white on black are the amino acid residues identical to both amino acid sequences, and "-" indicates a gap in a sequence.

<6> Gene Cloning from Open Reading Frame AR15G-92

Using a forward primer composed of the nucleotide sequence represented by SEQ ID NO: 5 (5'-CACCAT-GAGAGCCTGGATCGCCGTA-3': 4 nucleotides (CACC) were added to the 5'-end of the nucleotide sequence represented by SEQ ID NO: 3, wherein the CACC added to the 5' side is a sequence to enable insertion into a vector), and a reverse primer composed of the nucleotide sequence represented by SEQ ID NO: 4 (5'-CTAAGGGTT-GCTTTCAGCAAAAG-3'), PCR was performed using the hot spring soil DNA that had been amplified by the genome DNA amplification kit (GenomiPhi V2 DNA Amplification Kit, manufactured by GE Healthcare, Inc.) as a template. The nucleotide sequence represented by SEQ ID NO: 3 is homologous (identical) with the partial sequence composed of the nucleotides from positions 1 to 21 of the nucleotide sequence represented by SEQ ID NO: 2. Further, the nucleotide sequence represented by SEQ ID NO: 4 is complementary with the partial sequence composed of the nucleotides from positions 757 to 780 of the nucleotide sequence represented by SEQ ID NO: 2. The amplified PCR product was inserted into a pET101/D-TOPO vector of a Champion pET Directional TOPO Expression Kit (manufactured by Life Technologies Inc.), and transformed into a One Shot TOP 10 strain. Positive clones were selected by colony PCR and cultured in an LB liquid medium containing 100 mg/L of ampicillin at a temperature of 37° C. and 200 rpm for 17 to 20 hours, and then plasmids were prepared using a miniprep kit (Wizard plus SV Minipreps DNA Purification System, manufactured by Promega Corporation). Sequence confirmation of the prepared plasmids was performed using a sequencer (3730 DNA Analyzer, manufactured by Life Technologies Corporation).

Three gene clones AR15G-92-3, AR15G-92-6 and AR15G-92-16 were obtained from the open reading frame AR15G-92 by PCR cloning. The nucleotide sequence of the endoglucanase candidate gene AR15G-92-6 included 780 bp in a similar manner to the open reading frame AR15G-92 (SEQ ID NO: 2), and these nucleotide sequences were completely identical.

<7> Gene Expression of AR15G-92-6 Gene and Purification of Enzymatic Protein

Following sequence confirmation, the plasmid having the target gene was introduced into E. coli for protein expression using the heat shock method. The Rosetta-gamiB (DE3) pLysS strain (manufactured by Merck) was used as the competent cell for the transformation. Expression of the target protein was induced by inoculating the E. coli having the target gene into an LB medium containing 100 mg/L of ampicillin, culturing to about OD600=0.2 to 0.8, subsequently adding IPTG (isopropyl-β-D(−)-thiogalactopyranoside), and performing additional culturing for 20 hours. Following completion of the culturing, the E. coli was collected by centrifugation, and an amount of 50 mM Tris-HCl buffer (pH 8.0) equivalent to 1/10 of the volume of the culture liquid was then added and suspended. Subsequently, a process consisting of 30 seconds disrupting and then 30 seconds of rest was repeated 10 times using an ultrasonic disrupter, BioRuptor UCD-200T (manufactured by Cosmo Bio Co. Ltd.), thus obtaining a crude extract of the gene recombinant E. coli containing the target protein. This gene recombinant E. coli crude extract was subjected to a heat treatment at 95° C. for 2 hours and then to centrifugation, and the resulting supernatant was used as a crude enzyme solution.

<8> Measurement of CMC Hydrolysis Activity of AR15G-92-6

First, the CMC hydrolysis activity of the enzymatic protein (AR15G-92-6) encoded by the AR15G-92-6 gene was investigated using CMC (carboxymethyl cellulose, manufactured by Sigma-Aldrich Co. LLC.) as a substrate.

The CMC hydrolysis activity of the crude enzyme solution obtained in section 7> above was measured by reacting a mixture solution composed of 50 µL of a 1% by mass CMC aqueous solution, 25 µL of a 200 mM acetate buffer (pH 5.5), and 25 µL of the crude enzyme solution at a temperature of 50 to 130° C. for 20 or 30 minutes. In all measurements, a mixture solution prepared by replacing the crude enzyme solution with a 50 mM Tris-HCl buffer (pH 8.0) and then reacting the solution under the same conditions was used as a control. Further, the substrate solution and the mixture solution containing the buffer and the enzyme solution were held separately at the reaction temperatures for 5 minutes before being mixed to initiate the reaction. Following completion of the reaction, an equal volume of a 3,5-dinitrosalicylic acid reagent (DNS solution) was added thereto, and the resulting mixture was heated at 100° C. for 5 minutes, cooled on ice for 5 minutes, and then centrifuged at 17,500 g at room temperature for 5 minutes to obtain a supernatant. The amount of reducing sugars within the supernatant was determined by measuring the absorbance at 540 nm using a spectrophotometer, calculating the amount of reducing sugars using a calibration curve prepared with glucose, and then calculating the amount of reducing sugars produced by the enzymatic hydrolysis based on the difference from the control.

<9> Substrate Specificity of AR15G-92-6

The hydrolysis activity of the enzyme protein (AR15G-92-6) encoded by the AR15G-92-6 gene against various cellulose substrates and hemicellulose substrates was investigated. In the measurements, the crude enzyme solution obtained in section <7> above was used. For the substrates, CMC (manufactured by Sigma-Aldrich Co. LLC.), PSA, β-glucan derived from barley (manufactured by Megazyme, Inc.), Avicel powder (microcrystalline cellulose powder, manufactured by Merck & Co., Inc.), lichenan (manufactured by MP Biomedicals, LLC.), laminarin (derived from Laminaria digitata, manufactured by Sigma-Aldrich Co. LLC.), xylan (derived from birch wood, manufactured by Sigma-Aldrich Co. LLC.), PNPG (manufactured by Sigma-Aldrich Co. LLC.), PNPX (manufactured by Sigma-Aldrich Co. LLC.) and PNPC (manufactured by Sigma-Aldrich Co. LLC.) were used.

The PSA was prepared by first dissolving an Avicel powder (microcrystalline cellulose powder, manufactured by Merck & Co., Inc.) in a phosphoric acid solution, subsequently adding purified water to cause precipitation, and then washing until a pH of 5 or higher was reached. All the PSA used in the following experiments was prepared by this method.

Specifically, first, a reaction solution composed of a mixture solution containing 25 µL of a 200 mM acetate buffer (pH 5.5) and 25 µL of the crude enzyme solution was preincubated at 99° C. for 5 minutes. 50 µL of one of the substrate solutions (a 1% by mass aqueous solution in the case of CMC, PSA, β-glucan, Avicel powder, lichenan, laminarin or xylan, or a 3.4 mM aqueous solution in the case of PNPG, PNPX or PNPC) that had been held in the same manner was then added to the reaction solution, and the enzyme reaction was performed by incubating the resulting mixture solution at 99° C. for 20 minutes. In all measurements, a mixture solution prepared by replacing the crude enzyme solution with a 50 mM Tris-HCl buffer (pH 8.0) and then reacting the solution under the same conditions was used as a control.

Following completion of the reaction, in the case of those reactions performed using CMC, PSA, β-glucan, Avicel powder, lichenan, laminarin or xylan as the substrate, the same method as that described in section <8> above for investigating the CMC hydrolysis activity of AR15G-92-6 was used to determine the amount of reduced sugars produced by the hydrolysis.

However, in the case of xylan, a calibration curve prepared with xylose was used.

In the case of the reactions performed using PNPG, PNPX or PNPC as the substrate, following completion of the reaction, an equal volume of a 200 mM aqueous solution of sodium carbonate was added, and the resulting mixture was then centrifuged for 5 minutes to obtain a supernatant. The amount of p-nitrophenol in the supernatant was determined by measuring the absorbance at 420 nm using a spectrophotometer, calculating the amount of p-nitrophenol in the supernatant using a calibration curve prepared with p-nitrophenol, and then determining the amount of p-nitrophenol produced by the enzymatic hydrolysis on the basis of the difference from the control.

Each measurement was performed for three independent experiments, and a mean value and a standard error were determined. The hydrolysis activity against each substrate was shown as the relative value (relative activity in percentage (%)) with respect to the CMC hydrolysis activity which was defined as 100%. In other words, when the amount of reduced sugars produced by the reaction using CMC as a substrate was defined as 100%, the hydrolysis activity against each substrate was shown as the relative value (%) of the amount of reduced sugars or amount of p-nitrophenol which was produced by the reaction. The relative values (%) of the hydrolysis activity against various substrates are shown in FIG. 2. The results revealed that AR15G-92-6 exhibited hydrolysis activity against CMC, β-glucan, PSA, lichenan and Avicel, but exhibited very low hydrolysis activity against laminarin, xylan and PNPC, and exhibited almost no hydrolysis activity against PNPG and PNPX.

<10> Temperature Dependency of CMC Hydrolysis Activity

The temperature dependency of the CMC hydrolysis activity of the enzymatic protein (AR15G-92-6) was investigated. In the measurements, the crude enzyme solution obtained in section <7> above was used.

Specifically, the measurement was performed by reacting a mixture solution composed of 25 μL of a 200 mM acetate buffer (pH 5.5), 25 μL of the crude enzyme solution and 50 μL of a 1% by mass CMC aqueous solution at a temperature of 50, 60, 70, 80, 90, 95, 100, 110, 115, 120 or 130° C. for 20 minutes. When performing the activity measurement at a temperature of 100° C. or higher, a glass vial, a rubber stopper, and an aluminum seal (manufactured by Nichiden-Rika Glass Co., Ltd.) were used. Following completion of the reaction, the amount of reduced sugars produced by the enzymatic hydrolysis was determined in the same manner as in section <8> above. Each measurement was performed for three independent experiments, and a mean value and a standard error were determined.

Figure 3:
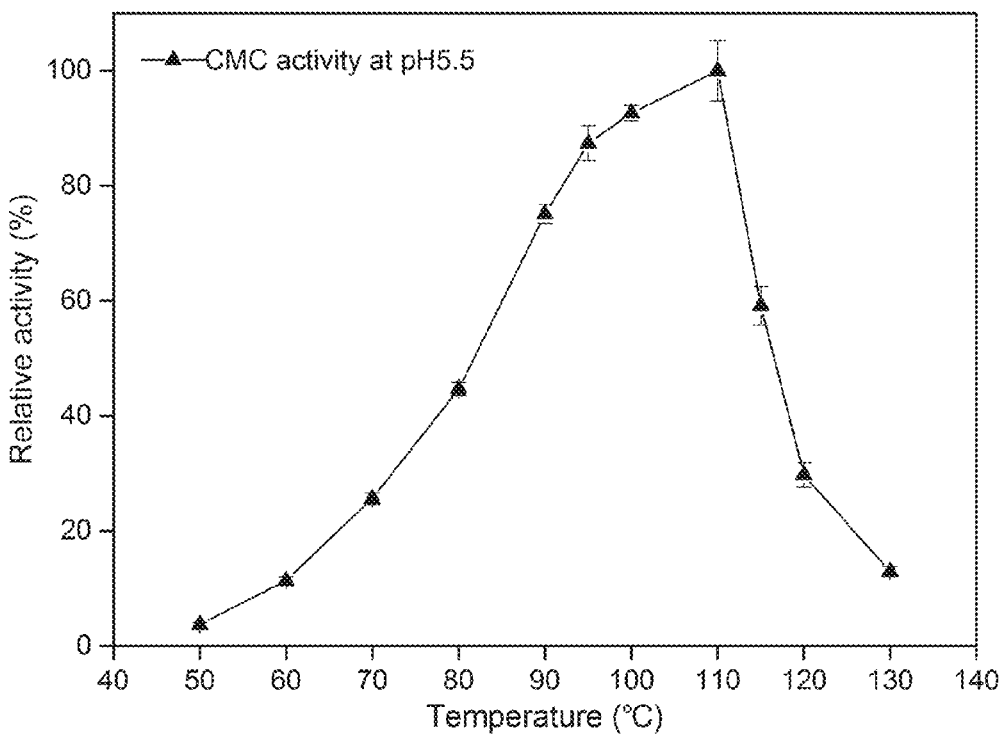
FIG. 3 is a diagram showing relative values (%) of the CMC hydrolysis activity (pH 5.5) of the AR15G-92-6 protein expressed in *E. coli* at various temperatures in Example 1.

The relative values (%) of the CMC hydrolysis activity at various temperatures, with respect to the CMC hydrolysis activity at a temperature of 110° C. which was defined as 100%, are shown in FIG. 3. AR15G-92-6 exhibited CMC degradation activity in a temperature range from 60 to 130° C. The optimum temperature ($T_{opt}$) at which the highest activity was observed was 110° C. at a pH of 5.5.

<11> pH Dependency of CMC Hydrolysis Activity

The pH dependency of the CMC hydrolysis activity of the enzymatic protein (AR15G-92-6) was investigated. In the measurements, the crude enzyme solution obtained in section <7> above was used. Further, as the buffer, a 200 mM glycine-hydrochloric acid buffer (pH 2.6 or 3.0), a 200 mM acetate buffer (SAB) (pH 3.5, 4.5, 5.0 or 5.5), a 600 mM GTA buffer (pH 6 to 10) or a 200 mM Britton-Robinson buffer (BR) (pH 8.0 or 9.0) was used.

Specifically, the measurement was performed by reacting a mixture solution composed of 25 μL of the buffer, 25 μL of the crude enzyme solution and 50 μL of a 1% by mass CMC aqueous solution at a temperature of 95° C. for 30 minutes. Following completion of the reaction, the amount of reduced sugars produced by the enzymatic hydrolysis was determined in the same manner as in section <8> above. Each measurement was performed for three independent experiments, and a mean value and a standard error were determined.

Figure 4:
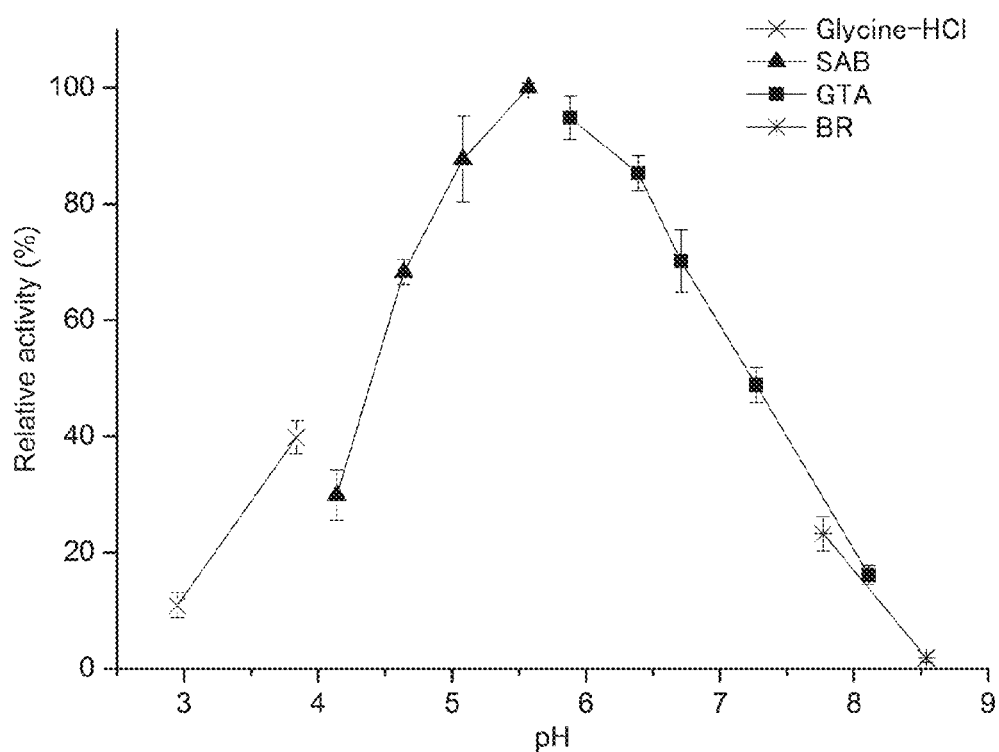
FIG. 4 is a diagram showing relative values (%) of the CMC hydrolysis activity (95° C.) of the AR15G-92-6 protein expressed in *E. coli* at various pH values in Example 1.

The relative values (%) of the CMC hydrolysis activity at various pH values, with respect to the CMC hydrolysis activity at a pH of 5.5 which was defined as 100%, are shown in FIG. 4. For the pH values, the actual measurement value obtained for the mixture solution containing the substrate, the buffer and the enzyme was plotted.

AR15G-92-6 exhibited CMC hydrolysis activity in a pH range from pH 3 to 8.

The optimum pH at 95° C. was pH 5.6 (actual measurement value obtained for the mixture solution containing the substrate, the buffer and the enzyme).

<12> Thermal Stability of AR15G-92-6 Using CMC as a Substrate

In order to investigate the thermal stability (heat resistance) of the enzymatic protein (AR15G-92-6), the enzyme was preincubated for 0 to 72 hours to determine the half-life ($T_{half}$) which is the preincubation time at which the enzyme activity was reduced to 50% of that of the control (preincubated for 0 hours). In the measurements, the crude enzyme solution obtained in section <7> above was used.

Specifically, first, a mixture solution composed of 25 μL of a 200 mM acetate buffer (pH 5.5) and 25 μL of the crude enzyme solution was preincubated by holding the temperature at 95° C. or 99° C. for 0, 3, 6, 24, 48 or 72 hours. Measurement of the CMC hydrolysis activity was performed by incubating the mixture solution following the preincubation and the 1% by mass CMC aqueous solution separately at 95° C. for 5 minutes, then adding an equal amount of the 1% by mass CMC aqueous solution to the mixture solution, and reacting the resulting mixture at 95° C. for 20 minutes. Following completion of the reaction, the amount of reduced sugars produced by the enzymatic hydrolysis was determined in the same manner as in section <8> above. Each measurement was performed for three independent experiments, and a mean value and a standard error were determined.

The CMC hydrolysis activity was shown as the relative value (%) assuming that the activity of the control was 100%.

Figure 5:
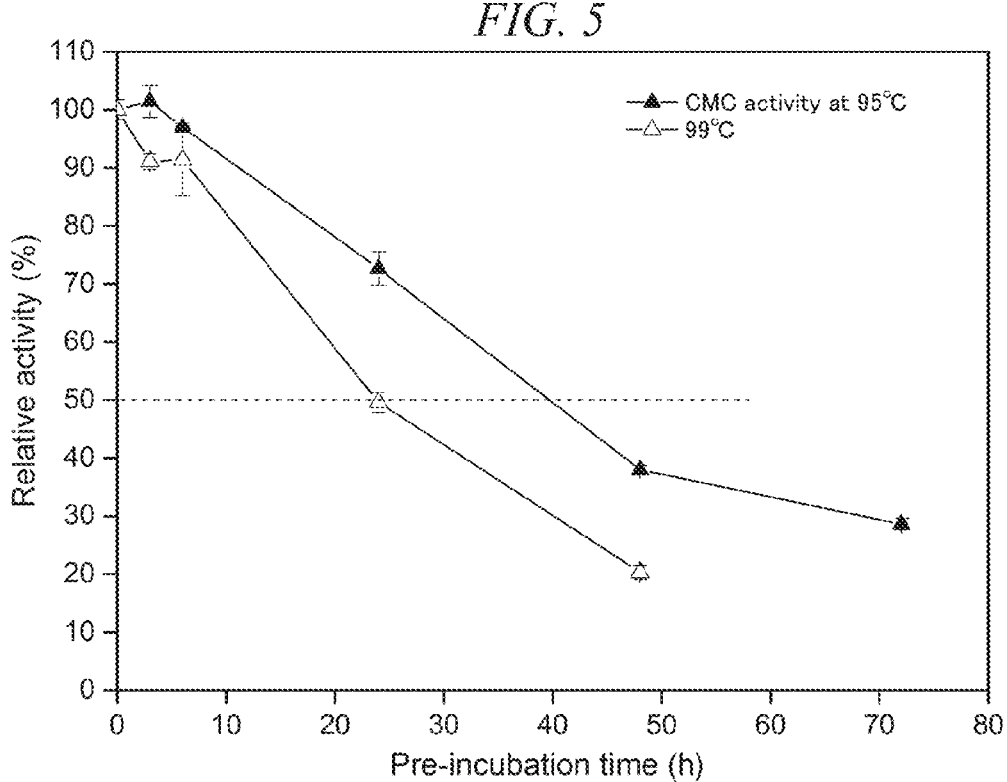
FIG. 5 is a diagram showing relative values (%) of the CMC hydrolysis activity of the AR15G-92-6 protein expressed in *E. coli*, at various preincubation time values at 95° C. or 99° C., in Example 1.

The relative values (%) of the CMC hydrolysis activity at various preincubation time values are shown in FIG. 5. The half-lives ($T_{half}$) of AR15G-92-6 at preincubation temperatures of 95° C. and 99° C. were approximately 40 hours and 24 hours, respectively.

What is claimed is:

1. An isolated recombinant hyperthermostable endoglucanase comprising:
   a polypeptide consisting of the amino acid sequence of SEQ ID NO: 1; and
   at least one moiety selected from the group consisting of a cellulose-binding module, a linker region, a signal peptide, and a tag.

2. A glycoside hydrolase mixture, comprising the hyperthermostable endoglucanase according to claim 1 and at least one other glycoside hydrolase.

3. A method for producing a lignocellulose degradation product, the method comprising producing a lignocellulose degradation product by bringing a lignocellulose-containing material containing cellulose into contact with the hyperthermostable endoglucanase according to claim 1.

4. A method for producing a lignocellulose degradation product, the method comprising producing a lignocellulose degradation product by bringing a lignocellulose-containing material containing cellulose into contact with the glycoside hydrolase mixture according to claim 2.

* * * * *

SEQUENCE LISTING

<160> NUMBER OF SEQ ID NOS: 6

<210> SEQ ID NO 1
<211> LENGTH: 259
<212> TYPE: PRT
<213> ORGANISM: Unknown
<220> FEATURE:
<223> OTHER INFORMATION: AR15G-92-6

<400> SEQUENCE: 1

Met Arg Ala Trp Ile Ala Val Ala Val Ala Ser Leu Leu Leu Leu
1               5                   10                  15

Thr Ala Ala Val Met Met Lys Arg Glu Glu Asn Lys Val Glu Gly
                20                  25                  30

Met Val Lys Leu Ser Gly Arg Trp Asp Cys Ile Asp Val Met Asn Gly
            35                  40                  45

Glu Tyr Arg Val Cys Asn Asn Val Trp Gly Ser Gly Glu Gly Val Gly
        50                  55                  60

Arg Gln Thr Ile Glu Val Asp Pro Phe Ser Thr Tyr Phe Lys Val Val
65                  70                  75                  80

Glu Thr Thr His Ser Ser Arg Gly Val Ala Ala Tyr Pro Phe Ile Tyr
                85                  90                  95

Lys Gly Cys His Trp Gly His Cys Thr Lys Asp Ser Gly Leu Pro Val
            100                 105                 110

Lys Val Arg Glu Leu Arg Ser Ala His Ser Thr Trp Ile Ile Ser Thr
        115                 120                 125

Ser Gly Val Glu Gly Thr Trp Asn Ala Ala Tyr Asp Ile Trp Phe Ser
130                 135                 140

Val Arg Gly Ala Ser Ser Pro Glu Gly Gly Ala Glu Leu Met Ile Trp
145                 150                 155                 160

Val Asn Arg Gly Gly Gly Ala Ala Pro Ala Gly Thr Lys Val Ala Thr
                165                 170                 175

Val Glu Val Gly Gly Tyr Glu Trp Asp Val Tyr Phe Phe Lys Met Asp
            180                 185                 190

Trp Asn Tyr Ile Ala Tyr Leu Ser Arg Arg Pro Leu Glu Arg Val Glu
        195                 200                 205

Leu Asp Ile Lys Ala Phe Ile Asp Asp Ala Leu Ser Arg Gly Tyr Ile
210                 215                 220

Asp Pro Glu Trp Tyr Leu Asp Ala Ile Glu Ala Gly Phe Glu Ile Trp
225                 230                 235                 240

Arg Gly Gly Ala Gly Leu Thr Thr Leu Arg Phe Ser Ala Phe Ala Glu
                245                 250                 255

Ser Asn Pro

<210> SEQ ID NO 2
<211> LENGTH: 780
<212> TYPE: DNA
<213> ORGANISM: Unknown
<220> FEATURE:
<223> OTHER INFORMATION: AR15G-92-6

<400> SEQUENCE: 2
atgagagcct ggatcgccgt agctgtagcg tcattgctgt tacttttgac ggccgctgta    60
atgatgaagc gagaagaaga gaacaaggtt gagggtatgg tgaagctctc aggcaggtgg   120
gattgcatcg acgtaatgaa tggagaatac agagtttgca acaacgtgtg gggctcggga   180
gagggtgtcg gcagacagac cattgaggtt gaccccttt cgacgtactt caaggttgtt   240

```
gaaactaccc acagctcaag aggggttgcc gcctatcctt tcatctacaa gggctgccac    300
tggggtcact gtacgaaaga tagcggctta cccgttaaag ttcgtgaact tcgctcagca    360
cactctacct ggataattag cacgagcggc gtagagggta cgtggaacgc cgcttacgat    420
atctggttca gcgtgagggg ggccagtagc ccggaaggag gggctgagct aatgatatgg    480
gttaacaggg gcggaggggc ggcgccagct ggtacgaaag tggctaccgt agaggtggga    540
gggtatgagt gggacgtcta cttcttcaag atggactgga attatatagc gtacctttca    600
aggcggccgc tggagcgcgt ggagctagat ataaaggcct tcatagacga tgcgctctcg    660
aggggctaca tagaccccga gtggtacttg gacgcgatag aagccgggtt cgagatctgg    720
aggggcggcg ccggtttaac caccttacga ttctcagctt tgctgaaag caacccttag    780
```

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Primer.

<400> SEQUENCE: 3

```
atgagagcct ggatcgccgt a                                              21
```

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Primer.

<400> SEQUENCE: 4

```
ctaagggttg ctttcagcaa aag                                            23
```

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Primer.

<400> SEQUENCE: 5

```
caccatgaga gcctggatcg ccgta                                          25
```

<210> SEQ ID NO 6
<211> LENGTH: 227
<212> TYPE: PRT
<213> ORGANISM: Rhodothermus marinus
<220> FEATURE:
<221> NAME/KEY: MISC_FEATURE
<222> LOCATION: (1)..(227)
<223> OTHER INFORMATION: Endoglucanase 12A (Cel12A)

<400> SEQUENCE: 6

```
Met Thr Val Glu Leu Cys Gly Arg Trp Asp Ala Arg Asp Val Ala Gly
1               5                   10                  15

Gly Arg Tyr Arg Val Ile Asn Asn Val Trp Gly Ala Glu Thr Ala Gln
            20                  25                  30

Cys Ile Glu Val Gly Leu Glu Thr Gly Asn Phe Thr Ile Thr Arg Ala
        35                  40                  45

Asp His Asp Asn Gly Asn Asn Val Ala Ala Tyr Pro Ala Ile Tyr Phe
    50                  55                  60
```

-continued

```
Gly Cys His Trp Gly Ala Cys Thr Ser Asn Ser Gly Leu Pro Arg Arg
65                  70                  75                  80

Val Gln Glu Leu Ser Asp Val Arg Thr Ser Trp Thr Leu Thr Pro Ile
                85                  90                  95

Thr Thr Gly Arg Trp Asn Ala Ala Tyr Asp Ile Trp Phe Ser Pro Val
            100                 105                 110

Thr Asn Ser Gly Asn Gly Tyr Ser Gly Gly Ala Glu Leu Met Ile Trp
        115                 120                 125

Leu Asn Trp Asn Gly Gly Val Met Pro Gly Gly Ser Arg Val Ala Thr
    130                 135                 140

Val Glu Leu Ala Gly Ala Thr Trp Glu Val Trp Tyr Ala Asp Trp Asp
145                 150                 155                 160

Trp Asn Tyr Ile Ala Tyr Arg Arg Thr Thr Pro Thr Thr Ser Val Ser
                165                 170                 175

Glu Leu Asp Leu Lys Ala Phe Ile Asp Asp Ala Val Ala Arg Gly Tyr
            180                 185                 190

Ile Arg Pro Glu Trp Tyr Leu His Ala Val Glu Thr Gly Phe Glu Leu
        195                 200                 205

Trp Glu Gly Gly Ala Gly Leu Arg Ser Ala Asp Phe Ser Val Thr Val
    210                 215                 220

Gln Lys Leu
225
```